(12) United States Patent
Netravali et al.

(10) Patent No.: US 12,364,658 B2
(45) Date of Patent: Jul. 22, 2025

(54) METHODS AND FORMULATIONS FOR CROSSLINKING HAIR OR OTHER KERATIN FIBERS USING OXIDIZED SUGARS AS CROSSLINKING AGENTS

(71) Applicant: CORNELL UNIVERSITY, Ithaca, NY (US)

(72) Inventors: Anil N. Netravali, Ithaca, NY (US); Namrata V. Patil, Sunnyvale, CA (US)

(73) Assignee: CORNELL UNIVERSITY, Ithaca, NY (US)

( * ) Notice: Subject to any disclaimer, the term of this patent is extended or adjusted under 35 U.S.C. 154(b) by 589 days.

(21) Appl. No.: 17/763,174

(22) PCT Filed: Sep. 28, 2020

(86) PCT No.: PCT/US2020/053156
§ 371 (c)(1),
(2) Date: Mar. 23, 2022

(87) PCT Pub. No.: WO2021/062407
PCT Pub. Date: Apr. 1, 2021

(65) Prior Publication Data
US 2023/0000748 A1  Jan. 5, 2023

Related U.S. Application Data

(60) Provisional application No. 62/906,679, filed on Sep. 26, 2019.

(51) Int. Cl.
*A61K 8/60* (2006.01)
*A45D 7/06* (2006.01)
(Continued)

(52) U.S. Cl.
CPC ............ *A61K 8/60* (2013.01); *A45D 7/06* (2013.01); *A61K 8/04* (2013.01); *A61Q 5/04* (2013.01); *A61Q 5/06* (2013.01)

(58) Field of Classification Search
None
See application file for complete search history.

(56) References Cited

U.S. PATENT DOCUMENTS

| | | |
|---|---|---|
| 5,258,501 A | 11/1993 | Barbaric et al. |
| 8,513,200 B2 | 8/2013 | Dixon et al. |

(Continued)

OTHER PUBLICATIONS

Dastidar, T.G. & Netravali, A.N., A soy flour based thermoset resin without the use of any external crosslinker, Green Chemistry, 15 (2013) pp. 3243-3251. (Year: 2013).*

(Continued)

*Primary Examiner* — Dominic Lazaro
(74) *Attorney, Agent, or Firm* — FisherBroyles, LLP; Andrew K. Gonsalves

(57) ABSTRACT

Disclosed is a method of crosslinking hair or other keratin fibers by (i) providing a crosslinking agent comprising an oxidized sugar having at least two aldehyde groups; and (ii) infiltrating a plurality of non-crosslinked hair or other keratin fibers with the crosslinking agent under conditions effective to cause protein molecules contained in the non-crosslinked hair or other keratin fibers to become crosslinked, thereby yielding a population of crosslinked hair or other keratin fibers. The protein molecules include amine groups that react with the aldehyde groups of the oxidized sugar to yield the crosslinked hair or other keratin fibers. Also disclosed are formulations for crosslinking hair or other keratin fibers and methods of using the formulations to treat human hair to maintain a desired three dimensional structure. This formulation includes a crosslinking agent having a plurality of oxidized sugars having at least two aldehyde groups or mixture thereof.

22 Claims, 3 Drawing Sheets

(51) Int. Cl.
  *A61K 8/04*   (2006.01)
  *A61Q 5/04*   (2006.01)
  *A61Q 5/06*   (2006.01)

(56) References Cited

U.S. PATENT DOCUMENTS

| | | | |
|---|---|---|---|
| 9,743,736 | B2 | 8/2017 | Malle et al. |
| 10,022,311 | B1 | 7/2018 | Esfahani et al. |
| 10,702,464 | B2 | 7/2020 | Fondin et al. |
| 11,013,306 | B2 | 5/2021 | Malle et al. |
| 11,019,902 | B2 * | 6/2021 | Netravali ............... A45D 7/06 |
| 2011/0256084 | A1 | 10/2011 | Dixon et al. |
| 2015/0174036 | A1 | 6/2015 | Washington et al. |
| 2015/0315249 | A1 | 11/2015 | Netravali et al. |
| 2017/0065049 | A1 * | 3/2017 | Netravali ............... C08H 1/06 |
| 2017/0095409 | A1 | 4/2017 | Yang et al. |

OTHER PUBLICATIONS

International Searching Authority (WO/ISA), International Search Report and Written Opinion issued in PCT counterpart PCT/US2020/053156, dated Feb. 8, 2021.
Patil et al., "Enhancing Strength of Wool Fiber Using a Soy Flour Sugar-Based 'Green' Cross-linker," ACS Omega, 4:5392-5401 (2019).
Pye et al., "Trehalose in hair care: Heat Styling benefits at high humidity," J. Cosmet. Sci., 63:233-241 (2012).
Williams et al., "Toward the Rational Design of Sustainable Hair Dyes Using Cheminformatics Approaches: Step 2. Identification of Hair Dye Substance Database Analogs in the Max Weaver Dye Library," ACS Sustainable Chem. Eng., 6:14248-14256 (2018).
Barma et al., "Natural Surfactants-Based Ag Nanofluids for Enhanced Wettability on Hair Surface," ACS Sustainable Chem. Eng., 6:3615-3623 (2018).
Pienpinijtham et al., "Analysis of cosmetic residues on a single human hair by ATR FT-IR microspectroscopy," Spectrochimica Acta Part A: Molecular and Biomolecular Spectroscopy, 197:230-236 (2018).
Miranda-Vilela et al., "An overview of chemical straightening of human hair: technical aspects, potential risks to hair fibre and health and legal issues," International Journal of Cosmetic Science, 36:2-11 (2014).
Cruz et al., "Changing the shape of hair with keratin peptides," RSC Adv., 7:51581-51592 (2017).
Song et al., "Effects of chemical structures of polycarboxylic acids on molecular and performance manipulation of hair keratin," RSC Adv., 6:58594-58603 (2016).
Dias et al., "Relaxing/straightening of Afro-ethnic hair: historical overview," J. Cosmetic Dermatology, 6:2-5 (2007).
Oiye et al., "Forensic Investigation of Formaldehyde in Illicit Products for Hair Treatment by DAD-HPLC: A Case Study," J. Forensic Sci., 61(4): 1122-1125 (2016).
Song et al., "Non-toxic and clean crosslinking system for protein materials: Effect of extenders on crosslinking performance," J. Cleaner Production, 150:214-223 (2017).
Xu et al., "Green Sustainable Technology for High-Efficiency and Low-Damage Manipulation of Densely Crosslinked Proteins," ACS Omega, 2:1760-1768 (2017).
Dastidar et al., "A soy flour based thermoset resin without the use of any external crosslinker," Green Chem., 15:3243-3251 (2013).
Jalaja et al., "Electrospun gelatin nanofibers: A facile cross-linking approach using oxidized sucrose," International Journal of Biological Macromolecules, 73:270-278 (2015).
Xu et al., "Correction: Potent and regularizable crosslinking of ultrafine fibrous protein scaffolds for tissue engineering using a cytocompatible disaccharide derivative," J. Mater. Chem. B, 8:7289-7290 (2020).
Xu et al., "Robust and Flexible Films from 100% Starch Cross-Linked by Biobased Disaccharide Derivative," ACS Sustainable Chem. Eng., 3:2631-2639 (2015).
Wang et al., "Effect of Surface Treatments on the Nanomechanical Properties of Human Hair," ACS Biomater. Sci. Eng., 4:3063-3071 (2018).
Bryant et al., "Hair Straightening," Chapter 30, pp. 262-268, Cosmetic Dermatology: Products and Procedures, Second Edition. Edited by Zoe Diana Draelos. John Wiley & Sons, Ltd. (2016).

* cited by examiner

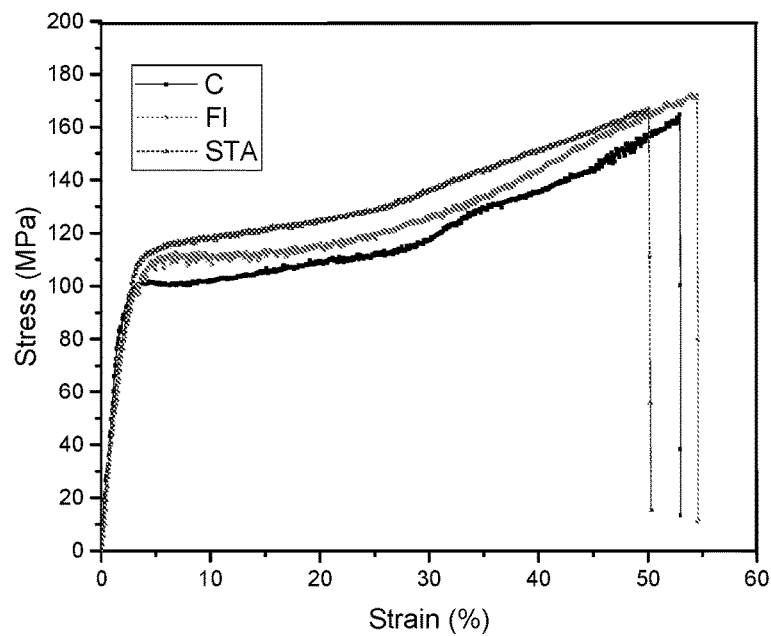
*FIG. 5*
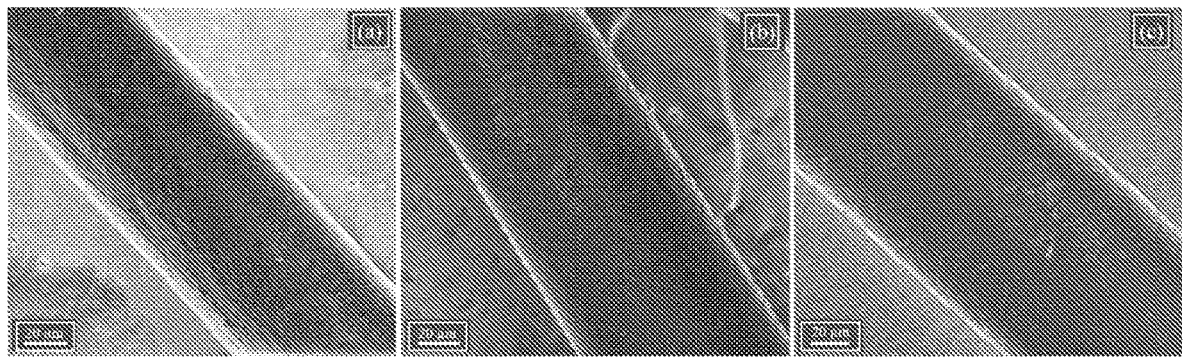
*FIG. 6A*  *FIG. 6B*  *FIG. 6C*

METHODS AND FORMULATIONS FOR CROSSLINKING HAIR OR OTHER KERATIN FIBERS USING OXIDIZED SUGARS AS CROSSLINKING AGENTS

CROSS-REFERENCE TO RELATED APPLICATIONS

This application is a U.S. National Phase filing under 35 U.S.C. § 371 of International Application No. PCT/US2020/053156, filed Sep. 28, 2020, and published as WO 2021/062407 A1 on Apr. 1, 2021, which claims priority benefit of U.S. Provisional Patent Application Ser. No. 62/906,679, filed Sep. 26, 2019, the disclosures of which are hereby incorporated by reference herein in their entirety.

FIELD OF THE DISCLOSURE

The present disclosure relates to, inter alia, a green technology involving the use of sugar-based crosslinkers for enhancing or improving physical appearance, straightening or curling efficiency, or hair styling durability of hair and other keratin fibers.

BACKGROUND OF THE DISCLOSURE

The haircare industry has been constantly growing and so have the number of products associated with haircare in the past couple of decades.[1] Hair styling is a major part of haircare which involves grooming the hair to achieve more manageable, frizz-free hair.[2] Hair straightening treatments are in vogue and require both chemical and heat treatments to achieve temporary to permanent hair straightening to achieve hair styling versatility.[2] Human hair is made up of keratin-based protein.[3] Keratin consists of amino acids linked by polypeptide bonds.[4-5] Polypeptide chains form an alpha helix structure which are twisted together to form microfibrils.[4] Many microfibrils together form a macrofibril. The inner layer of hair known as cortex is made-up cortical cells of macrofibrils and contributes to the strength, color and texture of the hair.[4] The cortex forms about 75% of the hair volume.[6] The outer layer of hair, cuticle, consists of scales which act as a preventive barrier for the cortex and, thus, protects the hair.[4-5]

There are a variety of treatments for hair straightening offered at present. Alteration of the cortex is important for straightening of hair.[5, 7-8] The most common method used for hair straightening is by using a flat iron.[6] Flat ironing process involves alterations of hydrogen bonds and salt linkages through heat and mechanical stress.[6] However, flat ironing manages to straighten the hair only temporarily as it can return back to its original state when exposed to high humidity or washing. Hair rebonding or chemical straightening are some of the other methods used to obtain more permanent straightening. In these processes strong chemical relaxers or reducing agents are used to break the disulfide bonds in the hair structure and then neutralizers or oxidizing agents are used to rebond the structure again.

Permanent straightening is achieved through the modification of covalent bonds. The relaxers used for breaking the bond are generally strong and alkaline in nature and can be hydroxide based (pH 13) or thio-based (pH 10).[9] 3.5% Sodium hydroxide (lye-based) or guanidine hydroxide activated with 4-7% calcium hydroxide, potassium hydroxide or lithium hydroxide (non-lye based) alkaline straighteners are commonly used by which the sulfur atom from a disulfide bond is removed and converted into a lanthionine bond creating a permanent non-reversible straightness.[6] Thio-based chemicals such as ammonium or ethanolamine thioglycolate and sulfites are commonly used reducing agents for hair which convert the disulfide bonds to sulfhydryl groups (chemical reduction) and further oxidized to reform the disulfide bonds at desired (straighter) conformation.[10-11]

Both hydroxide based lanthionization and thio-based reduction and oxidation techniques weaken and damage the hair permanently as it alters the cystine content or the disulfide bonds in the cortex and hydrolysis the peptide bonds.[6, 9] It also requires great amount of after-hair-care measures and results in hair thinning and dullness in the long run. These chemicals have a strong odor and can be irritating to skull skin or eyes during application. Thioglycolate and ammonium thioglycolate which are toxic and carcinogenic can be harmful if they get in contact with the skin.[9-10]

Besides the hydroxide and thio-based straighteners, formaldehyde and glutaraldehyde have been actively used for hair straightening, despite of being banned due to their toxicity, simply because they are inexpensive and result in shiny, straight hair by crosslinking the amine groups in the keratin peptide.[6] Formaldehyde is more dangerous as compared to glutaraldehyde as it causes serious damage to tissues and respiratory tracts of the users as well as the hairdressers working in salons and has been classified as a carcinogen.[6, 9, 12]

There have been some attempts to use non-toxic reducing agents to break the disulfide bond in the keratin and reform them to attain straightness. The use of cysteine as a 'green' reducing agent and use of polycarboxylic acids such as citric acid, butane tetra carboxylic acid (BTCA), malic acid and others to crosslink the hair have been studied.[2, 13-15] However, all these are two-step processes that still involve the reduction step (breaking of the disulfide bonds) which affects the strength of the hair permanently.

There is a need for new and improved technologies for enhancing and improving hair styling performance, including without limitation hair stabilizing attributes, of hair and other keratin fibers.

The present disclosure is directed to overcoming these and other deficiencies in the art.

SUMMARY

The present disclosure relates to, inter alia, a green technology involving the use of sugar-based crosslinkers for enhancing or improving physical appearance, straightening or curling efficiency, or hair styling durability of hair and other keratin fibers.

In one aspect, the present disclosure relates to a method of crosslinking hair or other keratin fibers. This method involves the steps of: (i) providing a crosslinking agent comprising an oxidized sugar having at least two aldehyde groups; and (ii) infiltrating a plurality of non-crosslinked hair or other keratin fibers with the crosslinking agent under conditions effective to cause protein molecules contained in the non-crosslinked hair or other keratin fibers to become crosslinked, thereby yielding a population of crosslinked hair or other keratin fibers. The protein molecules of the non-crosslinked hair or other keratin fibers comprise amine groups that react with the aldehyde groups of the oxidized sugar to achieve the crosslinking of the protein molecules to yield the crosslinked hair or other keratin fibers. In one embodiment of this method, the crosslinking agent is prepared according to a method involves the steps of: (i) providing a mixture of non-oxidized sugar molecules; and (ii) reacting the non-oxidized sugar molecules with a benign oxidizing agent to cause oxidation of the non-oxidized sugar molecules to yield a reaction mixture comprising oxidized sugar molecules having at least two aldehyde groups, said oxidized sugar molecules corresponding to the crosslinking agent.

In another aspect, the present disclosure relates to a formulation for crosslinking hair or other keratin fibers. This formulation includes a crosslinking agent having a plurality of oxidized sugars having at least two aldehyde groups or mixture thereof. The crosslinking agent is formulated so that the aldehyde groups of the oxidized sugars are effective to react with amine groups of protein molecules contained in a plurality of non-crosslinked hair or other keratin fibers to yield a population of crosslinked hair or other keratin fibers.

In another aspect, the present disclosure relates to a method of treating human hair to maintain a desired three dimensional structure. This method involves the steps of: (i) providing a formulation as disclosed herein; and (ii) treating a population of human hair with the formulation so as to maintain the desired three dimensional (3D) structure of the population of human hair. The human hair comprises non-crosslinked protein fibers having protein molecules having amine groups that react with the aldehyde groups of the oxidized sugar of the formulation.

Various aspects of the present disclosure are also addressed by the following Paragraphs 1-42 and in the noted combinations thereof, as follows:

Paragraph 1: A method of crosslinking hair or other keratin fibers, said method comprising: providing a crosslinking agent comprising an oxidized sugar having at least two aldehyde groups; and infiltrating a plurality of non-crosslinked hair or other keratin fibers with the crosslinking agent under conditions effective to cause protein molecules contained in the non-crosslinked hair or other keratin fibers to become crosslinked, thereby yielding a population of crosslinked hair or other keratin fibers, wherein the protein molecules of the non-crosslinked hair or other keratin fibers comprise amine groups that react with the aldehyde groups of the oxidized sugar to achieve the crosslinking of the protein molecules to yield the crosslinked hair or other keratin fibers.

Paragraph 2: The method according to Paragraph 1, wherein the hair or other keratin fibers comprise human hair, animal fibers, or a mixture thereof.

Paragraph 3: The method according to Paragraph 2, wherein the human hair is selected from the group consisting of straight hair, wavy hair, and curly hair, or variations thereof.

Paragraph 4: The method according to Paragraph 2, wherein the animal fibers are selected from the group consisting of wool, alpaca, angora, fur, cashmere, mohair, dog fur, and qiviut.

Paragraph 5: The method according to Paragraph 2, wherein the animal fibers are from animals selected from the group consisting of sheep, vicuna, alpaca, llama, muskox, goats, bison, camel, yak, horse, chinchilla, dog, and rabbit.

Paragraph 6: The method according to Paragraph 2, wherein the animal fibers have a form selected from the group consisting of raw fibers, yarns, felts, and woven or knitted fabrics.

Paragraph 7: The method according to Paragraph 1, wherein the sugar is selected from the group consisting of monosaccharides, disaccharides, trisaccharides, tetrasaccharides, and oligosaccharides, or mixtures thereof.

Paragraph 8: The method according to Paragraph 1, wherein the sugar is selected from the group consisting of galactose, sucrose, maltose, lactose, raffinose, and stachyose.

Paragraph 9: The method according to Paragraph 1, wherein the crosslinking agent is prepared according to a method comprising the steps of: providing a mixture of non-oxidized sugar molecules; and reacting the non-oxidized sugar molecules with a benign oxidizing agent to cause oxidation of the non-oxidized sugar molecules to yield a reaction mixture comprising oxidized sugar molecules having at least two aldehyde groups, said oxidized sugar molecules corresponding to the crosslinking agent.

Paragraph 10: The method according to Paragraph 9, wherein the oxidation is carried out at a neutral pH.

Paragraph 11: The method according to Paragraph 9, wherein the benign oxidizing agent is sodium periodate ($NaIO_4$).

Paragraph 12: The method according to Paragraph 1, wherein the crosslinking of the protein molecules is carried out at a neutral pH.

Paragraph 13: The method according to Paragraph 1, wherein the crosslinking agent primarily alters the amine groups of the keratin protein molecules, thereby leaving other groups of the keratin protein molecules unaltered.

Paragraph 14: The method according to Paragraph 1, wherein pairs of adjacent aldehyde groups in the oxidized sugar are directly linked by —$CR_1R_2$—O—$CR_3R_4$— or —$CR_1R_2$—O—$CR_3R_4$—$CR_5R_6$—, wherein $R_1$, $R_2$, $R_3$, $R_4$, $R_5$ or $R_6$ is selected from H, —$CH_2OH$, $C_1$-$C_3$ alkyl group, or a moiety of an oxidize sugar comprising aldehyde groups.

Paragraph 15: The method according to Paragraph 1, wherein pairs of adjacent aldehyde groups in the oxidized sugar have an average distance between two adjacent aldehyde groups of no more than the distance of —$CR_1R_2$—O—$CR_3R_4$— or —$CR_1R_2$—O—$CR_3R_4$—$CR_5R_6$—, wherein $R_1$, $R_2$, $R_3$, $R_4$, $R_5$ or $R_6$ is selected from H or —$CH_2OH$.

Paragraph 16: The method according to Paragraph 1, wherein at least 50% of the sugar rings are opened in the oxidized sugar.

Paragraph 17: The method according to Paragraph 1, wherein at least 75% of the sugar rings are opened in the oxidized sugar.

Paragraph 18: The method according to Paragraph 1, wherein at least 90% of the sugar rings are opened in the oxidized sugar.

Paragraph 19: The method according to Paragraph 1, wherein 100% of the sugar rings are opened in the oxidized sugar.

Paragraph 20: The method according to Paragraph 1, wherein the oxidized sugar comprises over 1.5 aldehyde groups per sugar unit on average.

Paragraph 21: The method according to Paragraph 1, wherein the oxidized sugar comprises at least 2 aldehyde groups per sugar unit on average.

Paragraph 22: The method according to Paragraph 1, wherein the oxidized sugar comprises less than 0.5 carboxyl group per sugar unit on average.

Paragraph 23: The method according to Paragraph 1, wherein the oxidized sugar comprises less than 0.2 carboxyl group per sugar unit on average.

Paragraph 24: The method according to Paragraph 1, wherein the oxidized sugar comprises no carboxyl group per sugar unit on average.

Paragraph 25: The method according to Paragraph 1, wherein the oxidized sugar has 2-10 sugar units.

Paragraph 26: The method according to Paragraph 1, wherein the crosslinking is carried out at neutral pH.

Paragraph 27: The method according to Paragraph 1, wherein the oxidized sugar crosslinks the hair or keratin fibers through the reaction between the aldehyde groups of the oxidized sugar and the amine groups of the keratin in hair fibers to form crosslinks, and wherein each oxidized sugar forming at least four covalent bonds linked to one or more molecules within hair or keratin fibers.

Paragraph 28: The method according to Paragraph 1, wherein the hair or keratin fibers are reshaped without breaking the disulfide covalent bonds in hair or keratin fibers.

Paragraph 29: The method according to Paragraph 1, wherein the hair or keratin fibers are treated or reshaped to be straight and a straightening efficiency of the hair or keratin fibers is stable and changed within 10% after at least 15 days.

Paragraph 30: The method according to Paragraph 1, wherein the hair or keratin fibers are treated or reshaped to be straight and a straightening efficiency of the hair or keratin fibers treated with the oxidized sugar is stable and is at least 95% of the original straightening efficiency after at least 4 washes.

Paragraph 31: The method according to Paragraph 1, wherein the hair or keratin fibers are treated or reshaped to be straight and a curly index of the hair or keratin fibers treated with the oxidized sugar is 1.00 after the first wash and is less than 1.05 after at least 4 washes.

Paragraph 32: The method according to Paragraph 1, wherein the hair or keratin fibers are treated or reshaped to be curly and a curly index of the hair or keratin fiber treated with the oxidized sugar is over 1.2 after at least 5 washes.

Paragraph 33: The method according to Paragraph 1, wherein the oxidized sugar has a structure of $$O{=}CH-(L-CR_0)_n-OH,$$

wherein:

L is selected from $-O-$, $-CR_1R_2-$, $-CR_1R_2-O-$, $-O-CR_1R_2-$, $-CR_1R_2-O-CR_3R_4-$, or any combination thereof, n is selected from any number in a range of 1 to 20, and $R_0$, $R_1$, $R_2$, $R_3$ or $R_4$ is selected from H, $-OH$, $-CH_2OH$, or a $C_1$-$C_3$ alkyl group, and wherein:

$R_0$ is different or identical in the n

units,

L is different or identical in the n

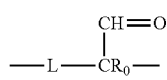

units, and $R_1$, $R_2$, $R_3$ or $R_4$ is different or identical in the n

units, respectively.

Paragraph 34: A formulation for crosslinking hair or other keratin fibers, said formulation comprising: a crosslinking agent comprising a plurality of oxidized sugars having at least two aldehyde groups or mixture thereof, wherein said crosslinking agent is formulated so that the aldehyde groups of the oxidized sugars are effective to react with amine groups of protein molecules contained in a plurality of non-crosslinked hair or other keratin fibers to yield a population of crosslinked hair or other keratin fibers.

Paragraph 35: The formulation according to Paragraph 34, wherein the formulation is in a form of a paste.

Paragraph 36: The formulation according to Paragraph 34, wherein the formulation is in a form of an aqueous solution.

Paragraph 37: A method of treating human hair to maintain a desired three dimensional structure, said method comprising the steps of: providing a formulation according to any one of Paragraphs 34-36; and treating a population of human hair with the formulation so as to maintain the desired three dimensional (3D) structure of the population of human hair, wherein the human hair comprises non-crosslinked protein fibers having protein molecules having amine groups that react with the aldehyde groups of the oxidized sugar of the formulation.

Paragraph 38: The method according to Paragraph 37, wherein the desired 3D structure of the human hair is selected from the group consisting of straight hair, wavy hair, and curly hair, or any variations thereof.

Paragraph 39: The method according to Paragraph 37, wherein the hair or keratin fibers are treated or reshaped to be straight and a straightening efficiency of the hair or keratin fibers is stable and changed within 10% after at least 15 days.

Paragraph 40: The method according to Paragraph 37, wherein the hair or keratin fibers are treated or reshaped to be straight and a straightening efficiency of the hair or keratin fibers treated with the oxidized sugar is stable and is at least 95% of the original straightening efficiency after at least 4 washes.

Paragraph 41: The method according to Paragraph 37, wherein the hair or keratin fibers are treated or reshaped to be straight and a curly index of the hair or keratin fibers treated with the oxidized sugar is 1.00 after the first wash and is less than 1.05 after at least 4 washes.

Paragraph 42: The method according to Paragraph 37, wherein the hair or keratin fibers are treated or reshaped to be curly and a curly index of the hair or keratin fiber treated with the oxidized sugar is over 1.2 after at least 5 washes.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, if provided, like reference numerals contained in the drawings are meant to identify similar or identical elements.

FIG. 5 is a graph illustrating typical stress-strain plots for C, FI and STA hair strands.

FIGS. 6A-6C are SEM images of C hair (FIG. 6A), FI hair (FIG. 6B), and STA hair (FIG. 6C).

DETAILED DESCRIPTION

Figure 1A:
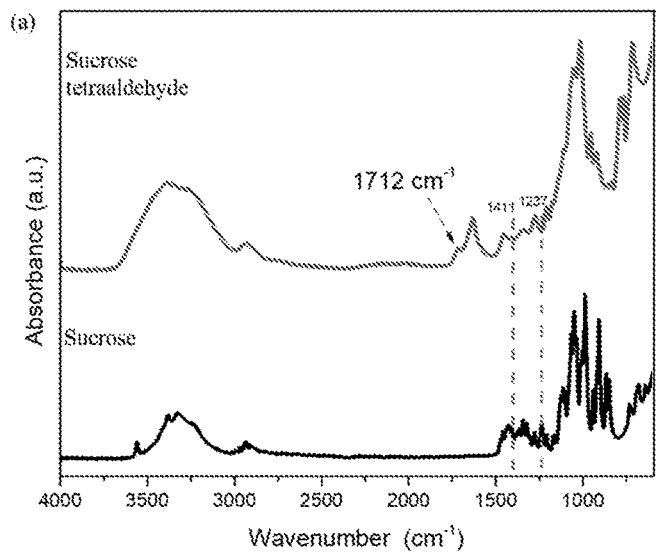
FIGS. 1A-1B are graphs showing ATR-FTIR results of sucrose and ST (FIG. 1A) and $^1$H-NMR results of sucrose and ST (FIG. 1B).

The present disclosure relates to, inter alia, a green technology involving the use of sugar-based crosslinkers (e.g., sugar-based aldehydes) for enhancing or improving physical appearance, straightening or curling efficiency, or hair styling durability of hair and other keratin fibers. The sugar-based crosslinkers of the present disclosure are particularly useful in treating human hair, although the present disclosure is not meant to be limited to human hair, but can also apply to other keratin fibers.

The present disclosure relates to, inter alia, a green technology for crosslinking protein molecules for various uses, where the protein molecules can be contained in protein fibers such as, but not limited to, human hair, animal fibers, and mixtures thereof. The green technology of the present disclosure provides crosslinking agents, formulations, and methods of making and using such crosslinking agents and formulations. In regard to one particular advantage of the green technology of the present disclosure over the existing art of treating hair or animal fibers, the presently disclosed green technology does not require the use of harsh chemicals or harmfully high temperatures to achieve permanent or substantially improved permanence of the desired structural changes from the hair or animal fiber treatments. Provided below is a more detailed description of the various aspects of the green technology of the present disclosure.

As used herein, the term "protein fibers" refers to any fiber material that includes protein as a component of the fiber. Protein fibers of the present disclosure include, without limitation, any fibers that contain protein molecules, and particularly protein molecules that have amino acids with functional groups (e.g., amine groups) that can react with an aldehyde group (e.g., to form a bond or link). Non-limiting examples of amino acids with such suitable functional groups include amino acids such as arginine and lysine. Non-limiting examples of particular types of protein fibers of the present disclosure are keratin-containing fibers.

As provided herein, "keratin-containing fibers" can include, without limitation, human hair, animal fibers, or a mixture thereof. In accordance with the present disclosure, the human hair can be any type of hair, regardless of the color, three dimensional structure, age, texture, fineness, etc. In accordance with the present disclosure, the animal fibers can include, without limitation, wool, alpaca, angora, fur, cashmere, mohair, dog fur, qiviut, or mixtures and variations thereof. Non-limiting examples of animals that can provide the animal fibers of the present disclosure include animals such as sheep, vicuna, alpaca, llama, muskox, goats, bison, camel, yak, horse, chinchilla, dog, rabbit, or related species thereof. Further, as in accordance with the present disclosure, the animal fibers can have various forms, including, without limitation, forms such as raw fibers, yarns, felts, woven or knitted fabrics, and the like.

As used herein to describe human hair or animal fibers or animal fabrics, the term "three dimensional structure" (3D structure) refers to the structural shape of the hair, animal fiber, or animal fabric. Non-limiting examples of 3D structures of human hair can include straight hair, wavy hair, curly hair, kinky hair, or variations thereof. Non-limiting examples of 3D structures of animal fibers or animal fabrics can include forms such as creased fabrics, non-creased fabrics, pleated fabrics, flat fabrics, roughened surface fabrics, wrinkled fabrics, and variations thereof.

In one aspect, the present disclosure relates to a method of crosslinking hair or other keratin fibers. This method involves the steps of: (i) providing a crosslinking agent comprising an oxidized sugar having at least two aldehyde groups; and (ii) infiltrating a plurality of non-crosslinked hair or other keratin fibers with the crosslinking agent under conditions effective to cause protein molecules contained in the non-crosslinked hair or other keratin fibers to become crosslinked, thereby yielding a population of crosslinked hair or other keratin fibers. The protein molecules of the non-crosslinked hair or other keratin fibers comprise amine groups that react with the aldehyde groups of the oxidized sugar to achieve the crosslinking of the protein molecules to yield the crosslinked hair or other keratin fibers.

As used herein, the term "infiltrating" generally refers to a process by which a crosslinking agent infiltrates hair or other keratin fibers so as to allow the crosslinking agent to react with the protein molecules contained in the hair or other keratin fibers. Once the crosslinking agent reacts with the protein molecules, the protein molecules can then be crosslinked, thereby resulting in hair or other keratin fibers that are then considered crosslinked. The term "diffusion" can also be used to describe this infiltrating or infiltration of the crosslinking agent into the hair or other keratin fibers.

In one embodiment, the infiltrating step is carried out at room temperature. In other embodiments, the infiltrating steps is carried out at temperatures ranging from between about 21° C. and about 220° C. In a particular embodiment, the infiltrating step is carried about at about 180° C. In a particular embodiment of this method, the infiltrating step is carried out at a temperature selected from the group consisting of less than, 220° C., less than 200° C., less than 190° C., less than 180° C., less than 170° C., less than 160° C., less than 150° C., less than 140° C., less than 130° C., and less than 120° C., less than 110° C., less than 100° C., less than 90° C., less than 80° C., less than 70° C., less than 60° C., less than 50° C., less than 40° C., less than 30° C., and less than 20° C., and for a length of time sufficient to yield the population of crosslinked hair or other keratin fibers at said temperature used for carrying out the infiltrating step. Generally, the lower the temperature, the longer the time is needed for infiltration or diffusion to occur.

In certain embodiments, the length of time the infiltrating step can be at least 1 minute, at least 5 minutes, at least 10 minutes, at least 15 minutes, at least 30 minutes, and at least 60 minutes. Non-limiting examples of suitable infiltration times can range from seconds to hours, including, for example, a range of less than a minute to less than 10 minutes, as well as a range of about 10 minutes to 4 hours or more, depending on the temperature used. In a particular embodiment, the infiltrating step is carried out at about 180° C. for about 8 minutes.

In a particular embodiment of this method, the heating step is carried out by applying a source of heat to the population of crosslinked hair or other keratin fibers. As used herein, the concept of "heating" the hair or other keratin fibers is meant to refer to the process of subjecting the hair or other keratin fibers to a particular raised temperature. Therefore, when describing the temperature of the heating step, reference is made to the "ambient temperature" and not the temperature of the hair or other keratin fibers themselves (e.g., human hair or animal fibers).

Non-limiting examples of the source of heat is for the heating step include sources such as a flat iron, hot rollers, a hot plate, a curling iron, a hair dryer, an iron, a clothes dryer, an oven, etc.

In another embodiment, this method further comprises washing the population of crosslinked hair or other keratin fibers to remove residual crosslinking agent or to remove crosslinking agent adhering to the hair or other keratin fibers, thereby substantially removing the crosslinking agent. In one particular embodiment, the washing is carried out using water or soap water. The soap water can include, without limitation, detergents, shampoo, and any other solution containing an agent effective to remove the residual crosslinking agent from the hair or other keratin fiber mixture or to remove crosslinking agent adhering to the hair or other keratin fibers.

In accordance with the present disclosure, examples of hair or other keratin fibers can include, without limitation, human hair, animal fibers, or a mixture thereof.

Various types of human hair can be used with the methods and formulations of the present disclosure. In certain embodiments, the human hair can include, without limitation, straight hair, wavy hair, curly hair, and variations thereof, as well as any other types of human hair.

Various types of animal fibers can be used with the methods and formulations of the present disclosure. In certain embodiments, the animal fibers can include, without limitation, wool, alpaca, angora, fur, cashmere, mohair, dog fur, qiviut, similar other types of animal furs.

Animal fibers from various animals can be used with the methods and formulations of the present disclosure. In certain embodiments, the animals can include, without limitation, sheep, vicuna, alpaca, llama, muskox, goats, bison, camel, yak, horse, chinchilla, dog, rabbit, and similar other types of animals.

Various forms of animal fibers can be used with the methods and formulations of the present disclosure. In certain embodiments, the animal fibers have a form that can include, without limitation, raw fibers, yarns, felts, woven or knitted fabrics, and similar other forms of animal fibers.

As described herein, the green technology of the present disclosure involves the use of a crosslinking agent. As used herein, the term "crosslinking agent" refers to an agent that includes an oxidized sugar, and particularly an oxidized sugar that includes at least two aldehyde groups. A suitable sugar of the oxidized sugar can include or be based on monosaccharides, disaccharides, trisaccharides, tetrasaccharides, and oligosaccharides. Non-limiting examples of particular types of sugars in accordance with the present disclosure include, without limitation, galactose, sucrose, maltose, lactose, raffinose, stachyose, and mixtures thereof. As used herein, the term "oligosaccharides" refers to sugars with 3-10 saccharide units (Moss et al., "Glossary of Class Names of Organic Compounds and Reactive Intermediates Based on Structure (IUPAC Recommendations 1995), *Pure & Appl. Chem.*, 67(8/9):1307-1375, 1353 (1995)).

In certain embodiments, the oxidized sugar has a structure of

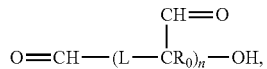

wherein:
L is selected from —O—, —CR$_1$R$_2$—, —CR$_1$R$_2$—O—, —O—CR$_1$R$_2$—, —CR$_1$R$_2$—O—CR$_3$R$_4$—, or any combination thereof,
n is selected from any number in a range of 1 to 20, and R$_0$, R$_1$, R$_2$, R$_3$ or R$_4$ is selected from H, —OH, —CH$_2$OH, or a C$_1$-C$_3$ alkyl group, and
wherein:
R$_0$ is different or identical in the n

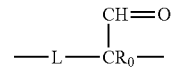

units,
L is different or identical in the n

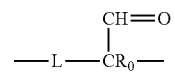

units, and
R$_1$, R$_2$, R$_3$ or R$_4$ is different or identical in the n

units, respectively.

In accordance with the present disclosure, the crosslinking of the protein molecules is carried out at a neutral pH.

In accordance with the present disclosure, the crosslinking agent primarily alters the amine groups of the keratin protein molecules, thereby leaving other groups of the keratin protein molecules unaltered.

In accordance with the present disclosure, pairs of adjacent aldehyde groups in the oxidized sugar are directly linked by —CR$_1$R$_2$—O—CR$_3$R$_4$— or —CR$_1$R$_2$—O—CR$_3$R$_4$—CR$_5$R$_6$—, wherein R$_1$, R$_2$, R$_3$, R$_4$, R$_5$ or R$_6$ is selected from H, —CH$_2$OH, C$_1$-C$_3$ alkyl group, or a moiety of an oxidize sugar comprising aldehyde groups.

In accordance with the present disclosure, pairs of adjacent aldehyde groups in the oxidized sugar have an average distance between two adjacent aldehyde groups of no more than the distance of —CR$_1$R$_2$—O—CR$_3$R$_4$— or —CR$_1$R$_2$—O—CR$_3$R$_4$—CR$_5$R$_6$—, wherein R$_1$, R$_2$, R$_3$, R$_4$, R$_5$ or R$_6$ is selected from H or —CH$_2$OH.

In accordance with the present disclosure, the oxidized sugars are in their respective closed-chain form, open-chain form, or both closed- and open-chain form. More particularly, the open-chain form can be partially or fully open. In certain embodiments, at least 5%, at least 10%, at least 15%, at least 20%, at least 25%, at least 30%, at least 35%, at least 40%, at least 45%, at least 50%, at least 55%, at least 60%, at least 65%, at least 70%, at least 80%, at least 85%, at least 90%, at least 95%, and/or 100% of the sugar rings are opened in the oxidized sugar.

In accordance with the present disclosure, the ratio of aldehyde groups per sugar unit in the oxidized sugar can be, without limitation, over 1.5 aldehyde groups per sugar unit on average. In certain embodiments of the methods and formulations of the present disclosure, the ratio of aldehyde groups per sugar unit in the oxidized sugar can be, without limitation, at least 2 aldehyde groups per sugar unit on average.

In accordance with the present disclosure, the ratio of carboxyl groups per sugar unit in the oxidized sugar can be, without limitation, less than 0.5 carboxyl groups per sugar unit on average. In certain embodiments of the methods and formulations of the present disclosure, the ratio of carboxyl groups per sugar unit in the oxidized sugar can be, without limitation, less than 0.2 carboxyl groups per sugar unit on average.

In accordance with the present disclosure, the oxidized sugar has no carboxyl groups per sugar unit on average.

In accordance with the present disclosure, the oxidized sugar may have 2-10 sugar units.

In accordance with the present disclosure, the crosslinking of the hair or other keratin fibers with the crosslinking agent is carried out at neutral pH.

In accordance with the present disclosure, the oxidized sugar may crosslink the hair or keratin fibers through the reaction between the aldehyde groups of the oxidized sugar and the amine groups of the keratin in hair fibers to form crosslinks. In certain embodiments, each oxidized sugar forms at least four covalent bonds linked to one or more molecules within hair or keratin fibers.

In accordance with the present disclosure, the hair or keratin fibers may be reshaped without breaking the disulfide covalent bonds in the hair or keratin fibers.

In accordance with the present disclosure, the hair or keratin fibers may be treated or reshaped to be straight, and a straightening efficiency of the hair or keratin fibers may be stable and changed within 10% after at least 15 days.

In accordance with the present disclosure, the hair or keratin fibers may be treated or reshaped to be straight, and a straightening efficiency of the hair or keratin fibers treated with the oxidized sugar may be stable and at least 95% of the original straightening efficiency after at least 4 washes.

In accordance with the present disclosure, the hair or keratin fibers may be treated or reshaped to be straight, and a curly index of the hair or keratin fibers treated with the oxidized sugar may be 1.00 after the first wash and may be less than 1.05 after at least 4 washes.

In accordance with the present disclosure, the hair or keratin fibers may be treated or reshaped to be curly, and a curly index of the hair or keratin fiber treated with the oxidized sugar may be over 1.2 after at least 5 washes.

In accordance with the present disclosure, the crosslinking agent used in the methods and formulations described herein may be prepared according to a method that involves the steps of: (i) providing a mixture of non-oxidized sugar molecules; and (ii) reacting the non-oxidized sugar molecules with a benign oxidizing agent to cause oxidation of the non-oxidized sugar molecules to yield a reaction mixture having oxidized sugar molecules that have at least two aldehyde groups. The oxidized sugar molecules correspond to the crosslinking agent as described herein. In certain embodiments of this method of preparing the crosslinking agent, the oxidation is carried out at a neutral pH. In certain embodiments of this method of preparing the crosslinking agent, the benign oxidizing agent is sodium periodate ($NaIO_4$).

The oxidation may be carried out at any temperature for any length of time suitable for the benign oxidizing agent to yield the crosslinking agent of the present disclosure.

In one embodiment, the oxidation is carried out at room temperature. In other embodiments, the oxidation is carried out at temperatures less than or greater than room temperature.

In certain embodiments, the oxidation is carried out for at least 1 minute, at least 5 minutes, 10 minutes, at least 30 minutes, at least 60 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours.

In certain embodiments, the oxidation is carried out in darkness, including, for example, in complete or substantially complete dark. In other embodiments, the oxidation is carried out in the presence of light, including partial or full lighting conditions.

In certain embodiments, the pH of the crosslinking agent is adjusted to a neutral (e.g., pH 7). However, a suitable pH can be more acidic or more basic than pH 7.

The oxidation may be carried out with stirring, including, without limitation, with gentle stirring. In certain embodiments, the stirring can be around or equal to 200 rpm, although stirring may also be at less than or greater than 200 rpm. In a certain embodiment, the oxidation can take place at room temperature for about 16 hours with gentle stirring at 200 rpm.

In certain embodiments, the oxidation reaction can be stopped by chemical reactions as contemplated and disclosed herein. In a particular embodiment, the benign oxidizing agent is $NaIO_4$, and the oxidation reaction is stopped using $BaCl_2$, which reacts with $NAIO_3$ to form $Ba(IO_3)_2$. After addition of $BaCl_2$, the solution can be stirred for about 5 minutes and placed in a refrigerator for about 1 hour to allow precipitation of $Ba(IO_3)_2$. After about 1 hour, the solution can be filtered to separate the insolubilized $Ba(IO_3)_2$ from the sucrose solution, e.g., a sucrose tetraaldehyde (ST) solution. If the sucrose solution is acidic, the pH of the sucrose solution (e.g., sucrose tetraaldehyde) can be adjusted to 7 using NaOH before the hair or other keratin fiber treatment.

In another aspect, the present disclosure relates to a formulation for crosslinking hair or other keratin fibers. This formulation includes a crosslinking agent having a plurality of oxidized sugars having at least two aldehyde groups or mixture thereof. The crosslinking agent is formulated so that the aldehyde groups of the oxidized sugars are effective to react with amine groups of protein molecules contained in a plurality of non-crosslinked hair or other keratin fibers to yield a population of crosslinked hair or other keratin fibers.

In accordance with the present disclosure, the formulation can be of various forms. In one embodiment, the formulation is in a form of a paste. In another embodiment, the formulation is in a form of an aqueous solution.

In one embodiment, the crosslinking agent is an aqueous solution having at least 1-60 weight percent of the oxidized sugar.

In another aspect, the present disclosure relates to a method of treating human hair to maintain a desired three dimensional structure. This method involves the steps of: (i) providing a formulation as disclosed herein; and (ii) treating a population of human hair with the formulation so as to maintain the desired three dimensional (3D) structure of the population of human hair. The human hair comprises non-crosslinked protein fibers having protein molecules having amine groups that react with the aldehyde groups of the oxidized sugar of the formulation.

In accordance with this method, suitable examples of the desired 3D structure of the human hair can include, without limitation, straight hair, wavy hair, curly hair, or any variations thereof. As mentioned above, in accordance with the present disclosure, the hair or keratin fibers may be treated or reshaped to be straight, and a straightening efficiency of the hair or keratin fibers may be stable and changed within 10% after at least 15 days. Furthermore, the hair or keratin fibers may be treated or reshaped to be straight, and a straightening efficiency of the hair or keratin fibers treated with the oxidized sugar may be stable and at least 95% of the original straightening efficiency after at least 4 washes. In addition, the hair or keratin fibers may be treated or reshaped to be straight, and a curly index of the hair or keratin fibers treated with the oxidized sugar may be 1.00 after the first wash and may be less than 1.05 after at least 4 washes. Moreover, the hair or keratin fibers may be treated or reshaped to be curly, and a curly index of the hair or keratin fiber treated with the oxidized sugar may be over 1.2 after at least 5 washes.

Additional Embodiments of the Present Disclosure

In one aspect, the present disclosure teaches the development of a novel sucrose-based nontoxic keratin crosslinker used to straighten the hair. Sucrose was oxidized using sodium periodate ($NaIO_4$) to form sucrose tetraaldehyde (ST) as shown in the Scheme 1.

Scheme 1. Oxidation reaction of sucrose forming sucrose tetraaldehyde.

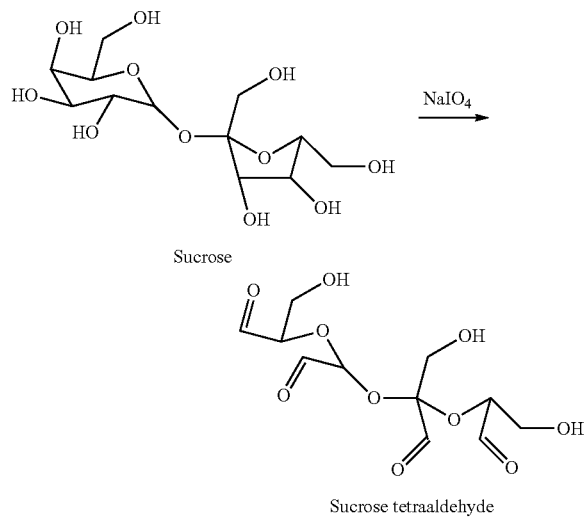

Sucrose

Sucrose tetraaldehyde

The four aldehyde groups generated on sucrose after oxidation can react with the amine groups present on the protein (keratin) molecules in the hair forming covalent crosslinks within the keratin. Crosslinking stabilizes the hair forming a 3D network and when straightened using a flat iron, the crosslinking can be completed which retains its straightness. The effect of ST treatment on durability of the straightness after exposure to high humid conditions and repeated shampoo washing was studied. While Brazilian natural curly hair was used in this straightening study, any other hair can be expected to perform similarly. Alternatively, this innovative green natural hair styling crosslinker could also be used to create curls on straight hair.

As discussed in more detail below, the sugar-based crosslinkers, methods, and products of the present disclosure have a number of features and advantages over existing technologies in the field.

In certain aspects and embodiments, the present disclosure involves the use of an oxidized sugar as a crosslinker, where the oxidized sugar has over 1.5 aldehyde groups per sugar unit. The present disclosure also provides for the use of a mixture of oxidized sugars as the crosslinkers, where the oxidized sugars in this mixture has an average of over 1.5 aldehyde groups per sugar unit.

As used herein, the term "sugar unit" refers to a single, simple sugar (monosaccharide) unit of the oxidized sugar of the present disclosure. As used herein, the term "simple sugar (monosaccharide)" refers to glucose, fructose, and galactose. In certain embodiments, the sugar has at least two sugar units. In certain other embodiments, the sugar has 2-10 sugar units, 2-9 sugar units, 2-8 sugar units, 2-7 sugar units, 2-6 sugar units, 2-5 sugar units, 2-4 sugar units, 2-3 sugar units, or 2 sugar units. As used herein, a disaccharide corresponds to a sugar having two sugar units, while an oligosaccharide corresponds to a sugar have 3-10 sugar units.

In certain embodiments, the oxidized sugar(s) have at least 2 (average) aldehyde groups per sugar unit.

In certain embodiments, no aldehyde group are located in a primary carbon of any oxidized sugar unit.

In certain embodiments, the crosslinking of hair is carried out at neutral pH as opposed to an alkaline pH. In certain embodiments, the crosslinker primarily alters the amine groups of a keratin protein leaving other groups unaltered as opposed to other treatments which involve the reduction of cystine groups (breaking the disulfide covalent bonds in hair).

In certain embodiments, the straightening efficiency of hair or keratin fibers treated with the oxidized sugar of the present disclosure is as stable as at least 85%, 87%, 90%, 95%, or greater for at least 10 days, at least 15 days, at least 20 days, at least 30 days, at least 45 days, at least 60 days, or greater.

In certain embodiments, there is substantially no change from day 2 up to day 45 in the straightening efficiency of hair or keratin fibers treated with the oxidized sugar of the present disclosure, which indicates the change of straightening efficiency from day 2 up to day 45 is within 10%, within 5%, within 2%, within 1%, etc. (see FIG. 4A).

Figure 4A:
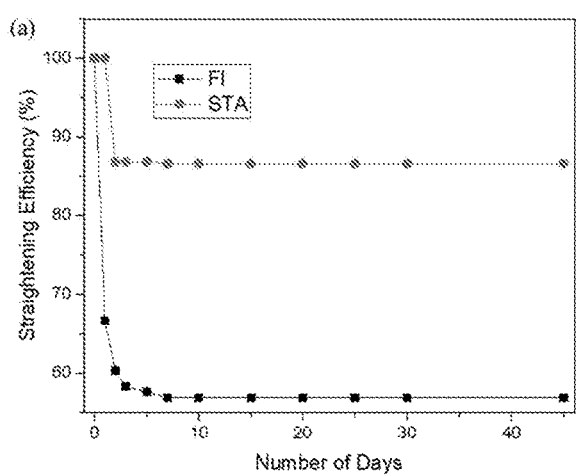
FIGS. 4A-4B are graphs illustrating straightening efficiency of the FI and STA hair hung at 21° C. and 65% as a function of the number of days (FIG. 4A) and the number of shampoo washes (FIG. 4B).
Figure 4B:
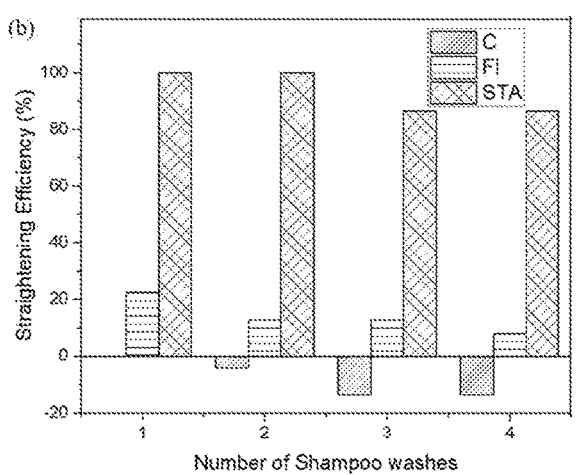

In certain embodiments, stable straightening efficiency of 100% is achieved in hair or keratin fibers treated with the oxidized sugar of the present disclosure after at least the first and at least second washes, with stable straightening efficiency being at least 92%, 95%, 98%, or 99% for at least 3, 4, or more washes (see FIG. 4B).

Figure 3:
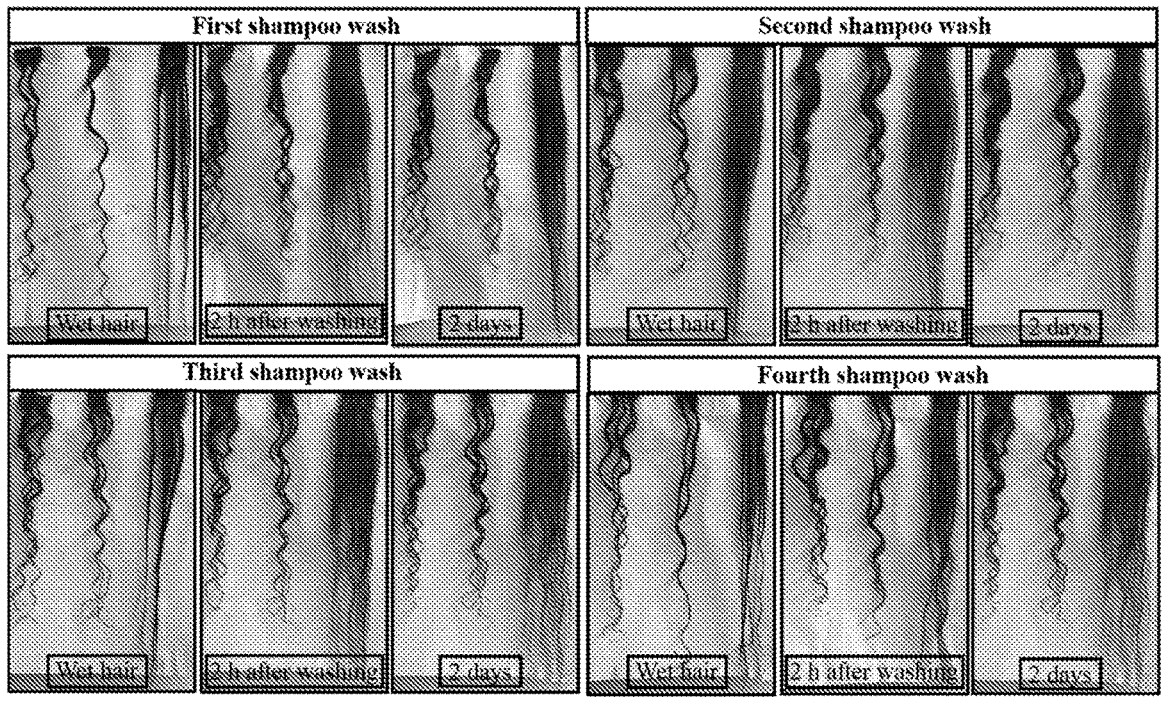
FIG. 3 are illustrations of C, FI and STA hair swatches from four, different shampoo wash samples (first, second, third, and fourth shampoo washes, as labeled). For each shampoo wash sample there are shown three sub-samples, which are shown from left to right as wet hair, 2 hours after washing, and 2 days after washing.

In certain embodiments, a stable curly index of 1.00 is achieved after the first and second wash of hair or keratin fibers treated with the oxidized sugar of the present disclosure, with the stable curly index of less than 1.01 (or 1-1.01), less than 1.02, or between 1-1.02 being achieved after at least 3 or at least 4 or more washes (see FIG. 3).

As used herein, "curly index" can be calculated as stretched length of hair/relaxed length of hair, or calculated as stretched length/relaxed length for a keratin fiber product. A curly index of 1.0 can represent a completely straight hair. A curly index of less than 1.05 can be considered as substantially straight for hair or a keratin fiber product. In some embodiments, a hair or keratin fiber with a curly index of over 1.1 or over 1.2 is treated with an oxidized sugar of the present disclosure to be completely straight or substantially straight.

In certain embodiments, the treated hair or keratin fiber remains substantially straight after 1 wash, 2 washes, 3 washes, 4 washes, 5 washes, 10 washes, 15 washes, or 30 washes. In particular embodiments, the treated hair remains substantially straight for at least 4 shampoo washes when subjected to conditioning at a relative humidity of 65%.

In other embodiments, a completely straight or substantially straight hair or keratin fiber, or a hair or keratin fiber with a curly index of less than 1.05 or less than 1.01, is treated with an oxidized sugar of the present disclosure and a hair styling device (e.g., a curly hair iron) to become curly or have a curly index of over 1.1, over 1.2, or over 1.3. In certain embodiments, the treated hair or keratin fiber remains curly or has a curly index of over 1.1, over 1.2, or over 1.3 after 1 wash, 2 washes, 3 washes, 4 washes, 5 washes, 10 washes, 15 washes, or 30 washes.

In certain embodiments, the average distance between two adjacent aldehyde groups in an oxidized sugar of the present disclosure is no more than the distance of —C—O—C—. In certain embodiments, the adjacent two aldehyde groups in an oxidized sugar are directly linked by —C—O—C— or —C—O—C—C—.

In certain embodiments, neutral pH is used for hair application without losing hair strengthening efficiency and without causing damage on the surface of the hair after STA treatment. By contrast, certain existing technologies in the field have taught that a higher pH than neutral pH is preferred and that reducing the pH will result in a decrease of the hair straightening efficiency.

Various aspects, embodiments, techniques, and applications of the present disclosure can be implemented using methods, techniques, materials, and systems as described in International Application No. PCT/US2015/028959, filed May 1, 2015, and published as WO 2015/168662-A1 on Nov. 5, 2015, and entitled "Green Technology for Crosslinking Protein Molecules for Various Uses," the disclosure of which is hereby incorporated by reference herein in its entirety.

EXAMPLES

The following examples are intended to illustrate particular embodiments of the present disclosure, but are by no means intended to limit the scope of the present disclosure.

Example 1

Natural 'Green' Sugar-Based Treatment for Hair Styling
1. Abstract

A major drawback of the current hair styling treatments is that it involves the use of toxic carcinogens such as thioglycolates, sulfites, formaldehyde and others. Constant exposure to such chemicals is harmful for the person getting the hair treatment and certainly to the hairstylists performing the treatment. A new 'green' sugar-based hair styling treatment was developed in the present research. The chemical composition of the sugar-based crosslinker, studied using ATR-FTIR and $^1$H-NMR showed the presence of multiple aldehyde groups on sugar, which were then used to chemically react with the amine groups present in keratin protein in hair. The chemical crosslinking of keratin molecules was carried out using a flat iron which can be readily adopted for practical applications in hair styling treatments. The crosslinked hair swatches were hung at high humidity condition (65%) as well as repeatedly washed with shampoo to characterize the permanency of the treatment. The hair straightening treatment was found to be durable to high humidity and several shampoo washings. In addition, the tensile characteristics of the hair such tensile stress, strain and Young's modulus showed that the properties remained unaffected after the treatment. SEM images showed no surface damage to the scales. The natural sugar-based green crosslinker may also be used to create curls in the straight hair.

2. Materials and Methods

Materials. 100% virgin Brazilian natural curly human hair (7.5" curly length; 12" stretched length) sample was obtained from Amazon. Remington© flat iron with settings from 10 to 30 and Pantene© shampoo were purchased from local Target Store. Sodium periodate (NaIO$_4$)≥99% was bought from Acros Organics, Bound Brook, NJ Barium dichloride (BaCl$_2$) was purchased from VWR, Rochester, NY Sucrose powder and sodium hydroxide (NaOH) pellets were purchased from Sigma-Aldrich Chemical Co., Allentown, PA.

Preparation of Sucrose Tetraaldehyde (ST) Solution for Hair Treatment. Five g of sucrose was dissolved in 100 ml of DI water. Six g of NaIO$_4$ was added to the sucrose solution. Oxidation was carried out in complete dark at room temperature (RT) for 16 h with gentle stirring at 200 rpm. At the end of 16 h, 4 g of BaCl$_2$ was added to the solution to stop further oxidation. BaCl$_2$ reacts with NaIO$_3$ to form Ba(IO$_3$)$_2$ which is insoluble in water at lower temperatures. After addition of BaCl$_2$, the solution was stirred for 5 min and placed in a refrigerator for 1 h to allow precipitation of Ba(IO$_3$)$_2$. After 1 h, the solution was filtered to separate the insolubilized Ba(IO$_3$)$_2$ from the ST. At this time the pH of ST solution was observed to be around 3.5. The pH of the ST solution was adjusted to 7 using NaOH before the hair treatment.

Characterizations of ST Solution. The prepared ST solution for hair straightening was characterized using ATR-FTIR and $^1$H-NMR to analyze the functional chemical groups. The ATR-FTIR spectra were collected using Thermo Nicolet Magna-IR 560 spectrometer (Madison, WI) having a split pea accessory. Each scan was an average of 300 scans from 4000 cm$^{-1}$ to 500 cm$^{-1}$ wavenumbers. $^1$H NMR spectra were recorded on INOVA 400 spectrometer (Varian Inc., Palo Alto, CA) using D20 as a solvent.

Hair Straightening Treatment. A swatch of hair (7.5" in curly length and weighing 1.2 g) was washed with shampoo and air dried before the treatment. The washed swatch of hair was clamped onto an aluminum foil using a clip and the prepared ST solution was applied onto the curls of the hair using a hair dye brush. The hair dye brush was dipped in the prepared ST solution and smaller sections of hair were individually coated with the ST solution from top to bottom, using 3-4 strokes of brush of about 2 inches length. The brush was dipped in the ST solution multiple times to ensure that all the hair in the swatch were well coated or wetted with ST solution from all sides. The hair swatch was then allowed to dry for about 8 min and flat ironed for about 8 passes at the flat iron setting 25 which corresponded to 180° C. (the flat iron had 30 settings with highest temperature at 30 of 215° C.). ST solution was applied to the hair again and dried and flat ironed, as mentioned above. The straightened hair swatch was set aside for 10 min at room temperature (RT) before washing it off with tap water at RT and flat ironed again for another 4-5 passes, if the hair curls after washing. This ST solution treated hair was termed as STA. Another swatch of hair was washed with shampoo, air dried and flat ironed at iron setting 25 for 25-30 passes until straight without using ST solution. This swatch was termed at FI.

Characterizations of Hair. Since humidity affects the straightness and curliness of the hair, most of the hair characterizations were performed in a conditioning room maintained at standard conditions of 21° C. and 65% relative humidity (RH). The untreated control (C), FI and STA hair were hung in the same conditioning room (21° C. and 65% RH) for 15 days and pictures were taken at regular intervals to observe the effect of humidity on the hair.

One set of hair swatches (C, FI and STA) was washed with shampoo every two days and hung in the conditioning room and pictures were taken after washing, drying and two day after washing to mimic the real-life application. Straightening efficiencies (SE) for FI and STA hair specimens were calculated after measuring their lengths before and after treatments using a ruler and the number of curls (twists) and using the formula given in Equation 1.[9]

$$\text{Straightening efficiency (\%)} = 100 - \left( \frac{\frac{\text{number of twists}_{after\ treatment}}{\text{length of hair}_{after\ treatment}}}{\frac{\text{number of twists}_{before\ treatment}}{\text{length of hair}_{before\ treatment}}} \right) \times 100 \quad (1)$$

SE values were calculated for C, FI and STA treated hair as a function of days of exposure in conditioning room at 21° C. and 65% RH as well as shampoo washings.

Tensile properties of hair were characterized using an Instron universal testing machine, model 5566 (Instron Corp., Canton, MA). Individual hair specimens from various C, FI and STA swatches were mounted on rectangular paper tabs by securing the two ends with a self-adhesive tape. The diameter of every hair was measured using a calibrated optical microscope, Olympus, model BX51 (Melville, NY), at three different locations, and the average was used to calculate the tensile properties of individual hair. The hair specimens were also conditioned at 21° C. and 65% prior to testing. The tests were also conducted at 65±3% RH and 21±1° C. using a gauge length of 30 mm and a strain rate of 0.6 min-. Thirty single hair specimens were randomly chosen from top, middle and bottom parts of the swatches of each type (C, FI and STA) for testing and statistical analysis. For the FI and STA hair, 10 specimens were chosen from each of the three different swatches treated at different times using ST solutions prepared at different times to ensure reproducibility of the results.

The surface characterization of the C, FI and STA hair was performed using Zeiss Gemini 500 scanning electron microscope (Germany), and at 1 kV.

3. Results and Discussion

Figure 1B:
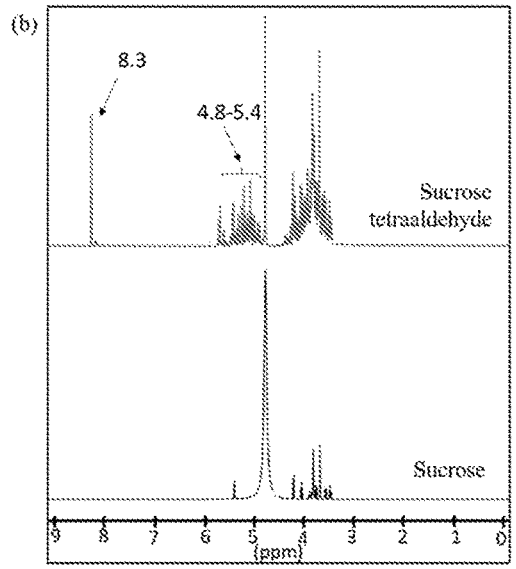

Characterization of ST Solution. FIG. 1A and FIG. 1B show the ATR-FTIR and $^1$H-NMR spectra of sucrose and the prepared ST solution. As seen in FIG. 1A, the spectrum of sucrose shows unique peaks associated with sucrose in the fingerprint region between 1500 cm$^{-1}$ to 700 cm$^{-1}$ wavenumbers. The peak at 907 cm$^{-1}$ corresponds to the C—H bending in sucrose. The peaks at 1049 cm$^{-1}$ and 1237 cm$^{-1}$ corresponds to the C—O stretch as well as C—C stretch in sucrose from C—OH groups while the peak at 1003 cm$^{-1}$ corresponds to the stretching if C—O band of the C—O—C linkage.[16] The peaks at 1322 cm$^{-1}$ and 1411 cm$^{-1}$ are due to 0-H bending of C—OH groups in sucrose. The ATR-FTIR spectra of the ST shows an additional peak at 1712 cm$^{-1}$. This peak corresponds to carbonyl groups formed as a result of oxidation of sucrose.[16-17] Similar peak at 1718 cm$^{-1}$ was seen by Jalaja and James after oxidizing sucrose using NaIO$_4$.[18] As seen in the spectrum of ST in FIG. 1A, the peak 1237 cm$^{-1}$ disappeared and the peak intensity of the one at 1411 cm$^{-1}$ reduced. Both of these peaks correspond to the C—OH bending in sucrose and the reduction in the peak intensity is the result of oxidation of hydroxyls to aldehyde groups. In both spectra (sucrose and ST), a peak around 3360 cm$^{-1}$ corresponds to the hydroxyl groups in the sucrose and the peaks between 2900 and 2700 cm$^{-1}$ correspond to the C—H stretch. The additional peak at 1630 cm$^{-1}$ in the ST is from the hydroxyl groups from water.

FIG. 1B shows the $^1$H-NMR spectra for sucrose and ST. The protons associated with sucrose are seen at 5.4 ppm and between 4.2 ppm and 3.2 ppm. The proton shift seen at 4.7 ppm in both spectra is a result of the D20 used as solvent. The proton shifts at 4 ppm and 4.2 ppm in sucrose are due to the protons from secondary hydroxyl groups present on the fructose ring in the sucrose. The three proton shifts associated with the three secondary hydroxyl groups on the glucose are seen between 3.5 and 3.75 ppm in sucrose. Fructose and glucose have two and three vicinal hydroxyl groups or secondary hydroxyl groups, respectively, which are cleaved due by NaIO$_4$ and oxidized to form two aldehyde groups on each fructose and glucose. This can be seen from the $^1$H-NMR of ST where an additional proton shift is clearly observed at 8.3 ppm due to the protons associated with the aldehyde groups created by oxidation.[17] The additional proton shifts between 4.8 and 5.5 ppm indicate the intermolecular acetal protons due to the hemiacetal formation.[17-20]

Figure 2A:
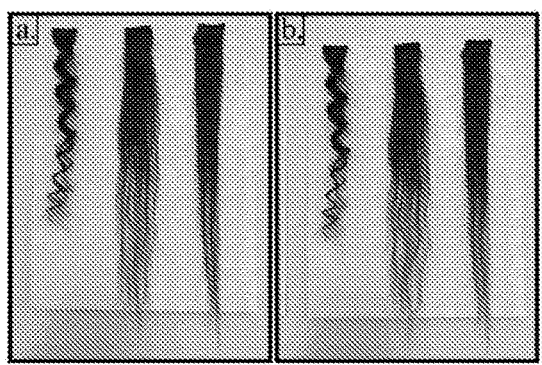
FIGS. 2A-2H are illustrations showing performance of C, FI and STA hair swatches in high humidity condition of 65% relative humidity after the following number of days: day 0 (FIG. 2A), day 1 (FIG. 2B), day 2 (FIG. 2C), day 3 (FIG. 2D), day 5 (FIG. 2E), day 7 (FIG. 2F), day 10 (FIG. 2G), and day 15 (FIG. 2H). The C, FI, and STA hair samples are shown in each figure from left to right.
Figure 2B:
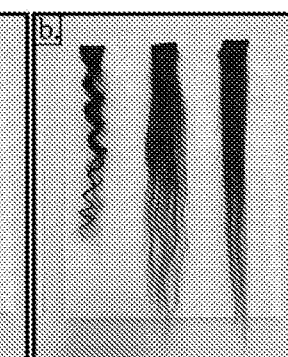
Figure 2C:
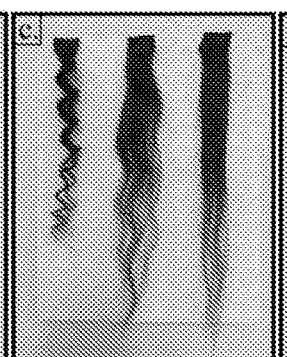
Figure 2D:
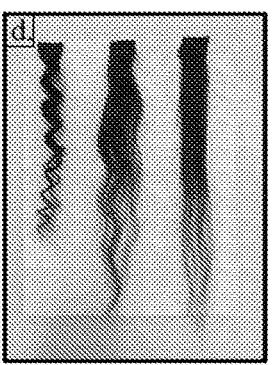
Figure 2E:
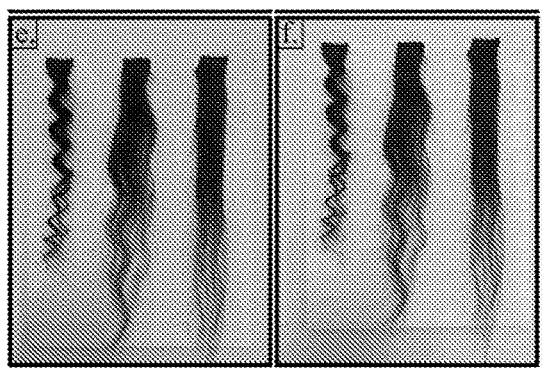
Figure 2F:
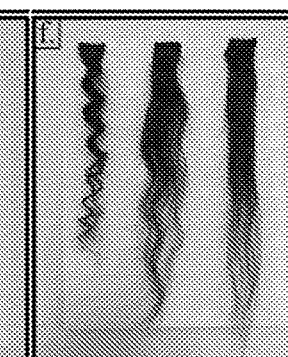
Figure 2G:
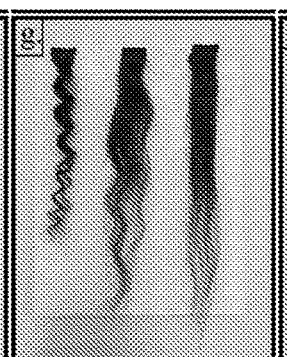
Figure 2H:
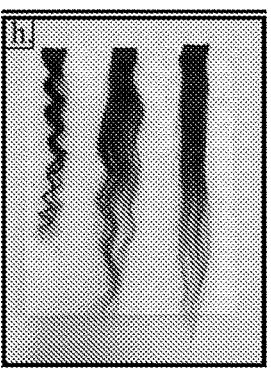

Characterization of Hair. FIGS. 2A-2H show pictures of C, FI and STA hair swatches, from left to right, respectively, taken from day 0 to day 15 exposure in conditioning room (65% RH), after the treatments. As seen in FIG. 2A, the control hair swatch showed 5 curls (each curl is counted as a z from top to bottom). Flat iron helps to straighten the curls as seen in FIG. 2A (0 day) and so does the STA treatment. As seen in FIG. 2B, the FI hair showed at least 1 curl at the bottom of the swatch after 1 day in the conditioning room at 21° C. and 65% RH while the STA hair maintained its straightness. FIG. 2C shows pictures of hair after 2 days in the conditioning room. It is clear that for the curl formed on after 1 day on the FI hair got enhanced and is now accompanied by 2 additional distinct curls. The STA hair, however, retained most of its straightness except for the bottom tip of the swatch after 2 days in conditioning room. The hair near the bottom of the swatch are fewer in number because of their unequal lengths and probably slip through the flat iron gap. As a result, it is possible that the fibers at the bottom of the swatch do not get adequate treatment as in the top and middle of the swatch. FIGS. 2D, 2E, 2F, and 2G show the pictures of hair swatches after 3, 5, 7, and 10 days, respectively. It was observed that the FI hair got fluffed-up showing at least 3 distinct curls while only the bottom tip of STA hair showed signs of curling. Most of the top hair of the STA hair showed perfect straightness. Similar effect was observed at the end of 15 days in the conditioning room (FIG. 2H). It was observed that the STA hair maintains its straightness for up to 45 days at 21° C. and 65% RH while the FI has the tendency to curl and frizz after just 2 days in the conditioning room. As mentioned earlier, the STA hair is well crosslinked due to the reaction of aldehyde groups from the ST solution and the amine groups from the keratin in hair. The amine groups from hair and aldehyde groups from sugar react to form a covalent bond via imine (Schiff base) formation.[17] Since the crosslinked molecules are unable to move, this provides the hair significant stabilization against the humidity. The FI hair on the other hand is just straightened due to the mechanical force and the heat applied due to flat ironing which involves rearrangement of hydrogen bonds. However, the newly formed hydrogen bonds from using a flat iron (heat and mechanical treatment) are susceptible to humid conditions and the hair tries reverts back to its original state over time.[21] Moisture from the conditioning room tends to easily plasticize the FI hair causing them to curl and fluff-up.[22] As four aldehyde groups are present on ST, it increases the potential crosslinking opportunities with the amine groups present in the keratin as compared to formaldehyde or glutaraldehyde which consists of one and two aldehyde groups respectively. Multiple intra and interfibrillar crosslinks can be formed with and within the cortex after ST treatment forming a dense 3D network which stabilizes the hair and helps retain its desired shape.

The C, FI and STA hair swatches were repeatedly washed using a warm 2% shampoo solution for 5 min and rinsed thoroughly under running water at RT until the lather was gone. The wet hair swatches were placed on a paper and hung on a wall in the conditioning room for 2 days before washing again. FIG. 3 shows the pictures of C, FI and STA hair swatches after 4 shampoo washes. Pictures of wet hair were taken immediately after washing. The second set of pictures in all of the shampoo washes were taken after 2 hours of drying in the conditioning room and the third one after 2 days in the conditioning room. As seen in FIG. 3, the control wet hair show 5 distinct curls when washed with shampoo. Upon drying for 2 hours in the conditioning room, the hair fluffs-up causing reduction in the length of the hair swatch and enhancing the curvature of the curls. The FI hair also immediately curled-up during the first shampoo wash while the STA hair remained straight after the first shampoo wash. Upon drying in the conditioning room after shampoo wash, the wet FI hair fluffed-up and the curvature of the curls increased. As a result, the length of the FI swatch reduced. The FI hair looked similar to the C hair as it regains all its original curls after the $1^{st}$ shampoo wash. As mentioned earlier, flat ironing only straightens the hair temporarily as it only involves alterations of hydrogen bonds and salt linkages.[21] The FI hair regained most of its original curl and the length decreased close to control hair. It was, however, observed that the STA hair maintained its straightness for 2 shampoo washes because of the covalent crosslinks formed which are more durable. As mentioned earlier, the 3D network formed within the cortex after crosslinking restricts the molecular movement or slippage and helps retain its shape. The STA hair was straight even after the third shampoo wash. It, however, started to curl around the bottom of the swatch while drying in the conditioning room. As mentioned earlier, the bottom part of the swatch is sparse and probably does not come in complete contact with the plates of the flat iron causing inadequate treatment. Because of the insufficient crosslinking, the moisture in the conditioning room causes the STA hair to begin to curl. At least 1 curl, with low curvature, was observed after the third and fourth shampoo wash while drying with negligible reduction in the overall length of hair swatch.

The straightening efficiency (SE) values were calculated for FI and STA hair swatches for up to 45 days of exposure to 65% RH and on C, FI and STA hair swatches after repeated shampoo washings for up to 4 washes, using Equation 1. FIG. 4A shows SE of FI and STA hair as a function of days the hair swatches were hung on a wall in conditioning room at 65% RH for up to 45 days. As seen in FIG. 4A, SE of FI and STA hair was 100% on day 0. After 1 day in the conditioning room, SE of the FI hair reduced to 66.7% while SE of STA hair was still 100%. At least 1 curl was observed in the FI hair after 1 day at 65% RH while the STA hair was fully straight (SE 100%). This can be clearly seen in FIG. 2B. SE of FI hair further reduced to 60.3% after 2 days in the at 65% RH when 3 curls developed on FI swatch while a slight curl in the bottom part of the STA hair was observed bringing down the efficiency of the STA hair to 86.8% after 2 days in the conditioning room. SE of the FI hair further reduced to 58.3% and 57.6% as the intensity of the curvature of the curls and the number of curls increased after 3 and 5 days in the conditioning room respectively. No additional curls were observed on the STA hair and its SE remained constant at 86.8% for up to 5 days in the conditioning room. SE of the FI hair further reduced to 56.9% after 7 days in the conditioning room and remained constant at 56.9% over time for up to 45 days. SE of STA hair was found to be 86.6% after 7 days in the conditioning room after which it remained unchanged for up to 45 days. Overall, SE of the STA hair was found to be much higher and more permanent compared to the FI hair.

FIG. 4B shows the SE (%) of C, FI and STA hair as a function of number of shampoo washes. It should be noted that each shampoo wash is accompanied by 2-day exposure to 65% RH at 21° C. As seen from FIG. 4B, the SE of FI hair reduced to 22.44% after the very $1^{st}$ shampoo wash. This implies that the FI hair regains most of it curls upon washing with shampoo. Again, this is because flat ironing is only a temporary way of hair straightening. Hair straightening using a flat iron only involves breaking and reforming of few hydrogen bonds in the keratin. These hydrogen bonds are weak and easily disrupted by water and, as a result, the FI hair reverts back to its original curly state after washing.[6] SE of the FI hair was found to decrease to 12.8% after $2^{nd}$ and $3^{rd}$ shampoo washes and down to just 8% after $4^{th}$ shampoo wash. This implies that the FI hair is as close to the original state or C hair after shampoo wash. It was also found that shampoo washing of the C hair introduces slight additional curls onto the swatch. Thus, SE of the C hair was negative. It was found to be −4.2% after 2 shampoo washes after which it remained constant at −13.6% after $3^{rd}$ and $4^{th}$ shampoo washes. The SE of STA hair was maintained at 100% for up to 2 shampoo washes after which it reduced to 86.6% after the $3^{rd}$ and $4^{th}$ shampoo washing. Overall, FIG. 4B shows that the SE of FI hair reduces significantly (as close to control) as the hair regains most of its curls after washing, while the SE of STA only reduces to 86.56% after 4 shampoo washes. This shows that the STA treatment is more durable than FI hair and can be used to attain permanent hair styling.

FIG. 5 shows the typical stress-strain plots for C, FI and STA hair specimens. As seen from FIG. 5, the typical stress-strain plots of the all hair show three distinct regions:

initial Hookean region, yield region and post yield region.[23] The tensile properties of the C, FI and STA hair are summarized in Table 1. As can be seen from FIG. 5, the Hookean region lies between 0%-5% tensile strain. The average tensile stress value of the C hair specimen at the end of the Hookean region was 103 MPa. In comparison, the average tensile stress value of the FI and STA hair specimens were observed to be 99.8 MPa and 99.7 MPa, respectively, indicating that the tensile stress of the FI and STA hair specimens in the Hookean region remained unchanged after treatments. The tensile strain of C, FI and STA hair specimens in the Hookean region was found to be 4.1%, 4.7%, 4.3%, respectively, which suggests that the properties of the FI and STA hair remained unchanged compared to C hair. The strain in the Hookean region comes from extension of weaker bonds such as hydrogen bonding within the amino acids, Van der Waals forces and coulombic interactions.[17] Immediately following the Hookean region the hair shows yielding behavior where large amount of strain is accompanied by very small rise in stress signifying very low modulus or high compliance. This yield region extends from 5% to 30% strain for all the hair specimens. It involves unfolding of the α-keratin into β-keratin configuration allowing larger deformation in the hair before breaking.[17, 23] Strain-hardening phenomenon was observed beyond the yield region for all fibers.[17, 23] Strain-hardening region extends from 30%-50% strain and ends upon the rupture of the hair. The breaking or ultimate fracture stress values for C, FI and STA hair specimens were found to be 164 MPa, 171 MPa, 166 MPa, respectively. These fracture stress values were found to be statistically insignificant, using an unpaired t-test, at a significance level of 0.05. This implies that the tensile stress of the hair strands was unaffected after flat ironing and the ST treatment. It is known that the keratin-based peptide in the hair is susceptible to thermal degradation after flat ironing which results in weakening the hair strands.[6] Continual heat treatments especially flat ironing in wet conditions increases the hair damage.[24] In the present study, flat ironing in the wet state was intentionally avoided, and the ST solution was allowed to dry before flat ironing the hair. While the pH of most commercial hair straightening products is highly alkaline (above 10), the pH of ST solution was adjusted to 7 to avoid alkaline denaturation of keratin peptides and retain tensile properties. Overall, the tensile results suggest that the tensile properties of the hair remained unchanged after the ST treatment and hence, could be a viable healthy alternative to currently used toxic hair crosslinkers. It is also clear from table 1 that the FI treatment reduces the initial modulus (Young's modulus) to 2.3 GPa compared to 2.6 GPa for C hair. However, after the STA treatment the modulus recovers back to 2.6 GPa as a result of the crosslinking.

scales on the surface. No visible change or damage to the scales can be observed after FI (FIG. 6B) or STA (FIG. 6C) treatments on the hair. Since excess heat from the flat iron can damage the hair, especially the scales, if done in the wet condition, care was taken to ensure that the hair was dry enough after treating with STA (by leaving them to air dry at RT for 10 min) before flat ironing. Most of the keratin crosslinking by ST solution occurs inside the hair as the ST molecule is small enough to penetrate the hair, leaving the surface of the hair undamaged after STA treatment.

4. Conclusions

The present study has successfully demonstrated that hair can be crosslinked using a 'green' sugar-based crosslinker. Sucrose was oxidized using $NaIO_4$ to convert the secondary hydroxyl groups to the aldehyde groups leading to a product with four aldehyde groups on sucrose (sucrose tetraaldehyde). Crosslinking of hair was carried out using chemical and mechanical treatment which involved diffusion of sucrose tetraaldehyde into the hair cortex along with flat ironing. The chemical crosslinking via covalent bond formation (imine) from the reaction of amine groups from keratin and aldehyde groups from sucrose resulted in a stable crosslinked 3D network within the hair cortex. The hair straightening process was optimized to achieve maximum straightening efficiency with the least damage to the tensile properties or the surface scales of the hair. The straightening was found to be stable up to 4 shampoo washings. These promising results open up a new 'green' innovative alternative of chemical treatment for hair styling without being exposed to currently used toxic, carcinogenic chemicals.

REFERENCES

Citation of a reference herein shall not be construed as an admission that such reference is prior art to the present invention. All references cited herein are hereby incorporated by reference in their entirety. Below is a listing of various references cited with respect to this example:
1. Williams, T. N.; Kuenemann, M. A.; Van Den Driessche, G. A.; Williams, A. J.; Fourches, D.; Freeman, H. S., Toward the rational design of sustainable hair dyes using cheminformatics approaches: step 1. database development and analysis. *ACS Sustainable Chemistry & Engineering* 2018, 6 (2), 2344-2352.
2. Dixon, F.; Pistorio, B.; Ellington, A.; Yee, M., Process for relaxing or straightening hair, using weak dicarboxylic acids with heat. Google Patents: 2013.
3. Deb Barma, S.; Banerjee, B.; Chatterjee, K.; Paria, S., Natural surfactants-based Ag nanofluids for enhanced wettability on hair surface. *ACS Sustainable Chemistry & Engineering* 2018, 6 (3), 3615-3623.

TABLE 1

Tensile properties of the C, FI and STA hair strands.

| | | Initial Hookean Region | | | Post Yield Region | |
|---|---|---|---|---|---|---|
| | Diameter (μm) | Stress (MPa) | Strain (%) | Young's Modulus (GPa) | Stress (MPa) | Strain (%) |
| C | 68.2 ± 11.9 | 103 ± 36.9 | 4.1 ± 0.6 | 2.6 ± 1.1 | 163.8 ± 54.8 | 49.3 ± 7.5 |
| FI | 73.3 ± 07.9 | 99.8 ± 34.3 | 4.7 ± 1.1 | 2.3 ± 1.0 | 171.0 ± 35.6 | 51.8 ± 8.6 |
| STA | 74.0 ± 16.0 | 99.7 ± 28.1 | 4.3 ± 1.4 | 2.6 ± 1.2 | 166.1 ± 44.0 | 49.7 ± 5.8 |

FIGS. 6A-6C show SEM images of C, FI and STA hair, respectively. As seen in FIG. 6A, the control hair shows 4. Pienpinijtham, P.; Thammacharoen, C.; Naranitad, S.; Ekgasit, S., Analysis of cosmetic residues on a single human hair by ATR FT-IR microspectroscopy. *Spectrochimica Acta Part A: Molecular and Biomolecular Spectroscopy* 2018, 197, 230-236.
5. Esfahani, J. M.; Luu, A.; Kluft, C., Keratin delivery process by reactive chemical composition for improved methods of strengthening and smoothing hair. Google Patents: 2018.
6. Miranda-Vilela, A.; Botelho, A.; Muehlmann, L., An overview of chemical straightening of human hair: technical aspects, potential risks to hair fibre and health and legal issues. *International journal of cosmetic science* 2014, 36 (1), 2-11.
7. Hair Straightening. In *Cosmetic Dermatology*, pp 262-269.
8. Fondin, T.; Sabbagh, A., Method for treating hair fibers. Google Patents: 2017.
9. Cruz, C. F.; Martins, M.; Egipto, J.; Osorio, H.; Ribeiro, A.; Cavaco-Paulo, A., Changing the shape of hair with keratin peptides. *RSC Advances* 2017, 7 (81), 51581-51592.
10. Song, K.; Xu, H.; Xie, K.; Yang, Y., Effects of chemical structures of polycarboxylic acids on molecular and performance manipulation of hair keratin. *RSC Advances* 2016, 6 (63), 58594-58603.
11. de Sá Dias, T. C.; Baby, A. R.; Kaneko, T. M.; Robles Velasco, M. V., Relaxing/straightening of Afro-ethnic hair: historical overview. *Journal of cosmetic dermatology* 2007, 6 (1), 2-5.
12. Oiye, E. N.; Ribeiro, M. F. M.; Okumura, L. L.; Saczk, A. A.; Ciancaglini, P.; de Oliveira, M. F., Forensic Investigation of Formaldehyde in Illicit Products for Hair Treatment by DAD-HPLC: A Case Study. *Journal of forensic sciences* 2016, 61 (4), 1122-1125.
13. Song, K.; Xu, H.; Mu, B.; Xie, K.; Yang, Y., Non-toxic and clean crosslinking system for protein materials: Effect of extenders on crosslinking performance. *Journal of Cleaner Production* 2017, 150, 214-223.
14. Xu, H.; Song, K.; Mu, B.; Yang, Y., Green and Sustainable Technology for High-Efficiency and Low-Damage Manipulation of Densely Crosslinked Proteins. *ACS omega* 2017, 2 (5), 1760-1768.
15. Malle, G.; Barbarat, P.; Pasini, I., Method for straightening keratinous fibers using heating means and malic acid. Google Patents: 2017.
16. Dastidar, T. G.; Netravali, A. N., A soy flour based thermoset resin without the use of any external cross-linker. *Green Chemistry* 2013, 15 (11), 3243-3251.
17. Patil, N. V.; Netravali, A. N., Enhancing Strength of Wool Fiber Using a Soy Flour Sugar-Based "Green" Cross-linker. *ACS Omega* 2019, 4 (3), 5392-5401.
18. Jalaja, K.; James, N. R., Electrospun gelatin nanofibers: a facile cross-linking approach using oxidized sucrose. *International journal of biological macromolecules* 2015, 73, 270-278.
19. Xu, H.; Liu, P.; Mi, X.; Xu, L.; Yang, Y., Potent and regularizable crosslinking of ultrafine fibrous protein scaffolds for tissue engineering using a cytocompatible disaccharide derivative. *Journal of Materials Chemistry B* 2015, 3 (17), 3609-3616.
20. Xu, H.; Canisag, H.; Mu, B.; Yang, Y., Robust and flexible films from 100% starch crosslinked by biobased disaccharide derivative. *ACS Sustainable Chemistry & Engineering* 2015, 3 (11), 2631-2639.
21. Krause, T.; Rust, R. C., hair styling: technology and Formulations. *Cosmetic Dermatology: Products and Procedures* 2016, 3, 270-279.
22. Pye, S.; Paul, P., Trehalose in hair care: heat styling benefits at high humidity. *Journal of cosmetic science* 2012, 63 (4), 233-241.
23. Feughelman, M., *Mechanical properties and structure of alpha-keratin fibres: wool, human hair and related fibres*. UNSW press: 1997.
24. Wang, N.; Barfoot, R.; Butler, M.; Durkan, C., Effect of Surface Treatments on the Nanomechanical Properties of Human Hair. *ACS Biomaterials Science & Engineering* 2018, 4 (8), 3063-3071.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Citation of a reference herein shall not be construed as an admission that such reference is prior art to the present invention. All references cited herein are hereby incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Illustrative embodiments of the processes, methods, and products of the present disclosure are described herein. It should be understood, however, that the description herein of the specific embodiments is not intended to limit the present disclosure to the particular forms disclosed but, on the contrary, the intention is to cover all modifications, equivalents, and alternatives falling within the spirit and scope of the invention by the appended claims. Thus, although the present invention has been described for the purpose of illustration, it is understood that such detail is solely for that purpose and variations can be made by those skilled in the art without departing from the spirit and scope of the invention which is defined by the following claims.

What is claimed is:

1. A method of crosslinking hair or other keratin fibers, said method comprising:
    providing a crosslinking agent comprising an oxidized sugar having at least two aldehyde groups; and
    infiltrating a plurality of non-crosslinked hair or other keratin fibers with the crosslinking agent under conditions effective to cause protein molecules contained in the non-crosslinked hair or other keratin fibers to become crosslinked, thereby yielding a population of crosslinked hair or other keratin fibers,
    wherein the protein molecules of the non-crosslinked hair or other keratin fibers comprise amine groups that react with the aldehyde groups of the oxidized sugar to achieve the crosslinking of the protein molecules to yield the crosslinked hair or other keratin fibers, and
    wherein at least 50% of the sugar rings are opened in the oxidized sugar.

2. The method according to claim 1, wherein the hair or other keratin fibers comprise human hair, animal fibers, or a mixture thereof.

3. The method according to claim 2, wherein the human hair is selected from the group consisting of straight hair, wavy hair, and curly hair, or variations thereof, or wherein the animal fibers are selected from the group consisting of wool, alpaca, angora, fur, cashmere, mohair, dog fur, and qiviut.

4. The method according to claim 2, wherein the animal fibers are from animals selected from the group consisting of sheep, vicuna, alpaca, llama, muskox, goats, bison, camel, yak, horse, chinchilla, dog, and rabbit.

5. The method according to claim 2, wherein the animal fibers have a form selected from the group consisting of raw fibers, yarns, felts, and woven or knitted fabrics.

6. The method according to claim 1, wherein the sugar is selected from the group consisting of monosaccharides, disaccharides, trisaccharides, tetrasaccharides, and oligosaccharides, or mixtures thereof.

7. The method according to claim 1, wherein the sugar is selected from the group consisting of galactose, sucrose, maltose, lactose, raffinose, and stachyose.

8. The method according to claim 1, wherein the crosslinking agent is prepared according to a method comprising:
    providing a mixture of non-oxidized sugar molecules; and
    reacting the non-oxidized sugar molecules with a benign oxidizing agent to cause oxidation of the non-oxidized sugar molecules to yield a reaction mixture comprising oxidized sugar molecules having at least two aldehyde groups, said oxidized sugar molecules corresponding to the crosslinking agent.

9. The method according to claim 8, wherein the benign oxidizing agent is sodium periodate ($NaIO_4$).

10. The method according to claim 1, wherein the crosslinking agent primarily alters the amine groups of the keratin protein molecules, thereby leaving other groups of the keratin protein molecules unaltered.

11. The method according to claim 1, wherein pairs of adjacent aldehyde groups in the oxidized sugar are directly linked by —$CR_1R_2$—O—$CR_3R_4$— or —$CR_1R_2$—O—$CR_3R_4$—$CR_5R_6$—, wherein $R_1$, $R_2$, $R_3$, $R_4$, $R_5$ or $R_6$ is selected from H, —$CH_2OH$, $C_1$-$C_3$ alkyl group, or a moiety of an oxidize sugar comprising aldehyde groups.

12. The method according to claim 1, wherein pairs of adjacent aldehyde groups in the oxidized sugar have an average distance between two adjacent aldehyde groups of no more than the distance of —$CR_1R_2$—O—$CR_3R_4$— or —$CR_1R_2$—O—$CR_3R_4$—$CR_5R_6$—, wherein $R_1$, $R_2$, $R_3$, $R_4$, $R_5$ or $R_6$ is selected from H or —$CH_2OH$.

13. The method according to claim 1, wherein the oxidized sugar comprises over 1.5 aldehyde groups per sugar unit on average.

14. The method according to claim 1, wherein the oxidized sugar comprises less than 0.2 carboxyl group per sugar unit on average.

15. The method according to claim 1, wherein the oxidized sugar has 2-10 sugar units.

16. The method according to claim 1, wherein the crosslinking is carried out at neutral pH.

17. The method according to claim 1, wherein the oxidized sugar crosslinks the hair or keratin fibers through the reaction between the aldehyde groups of the oxidized sugar and the amine groups of the keratin in hair fibers to form crosslinks, and wherein each oxidized sugar forms at least four covalent bonds linked to one or more molecules within hair or keratin fibers.

18. The method according to claim 1, wherein the hair or keratin fibers are reshaped without breaking the disulfide covalent bonds in hair or keratin fibers.

19. The method according to claim 1, wherein the oxidized sugar has a structure of

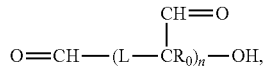

wherein:
    L is selected from —O—, —$CR_1R_2$—, —$CR_1R_2$—O—, —O—$CR_1R_2$—, —$CR_1R_2$—O—$CR_3R_4$—, or any combination thereof,
    n is selected from any number in a range of 1 to 20, and
    $R_0$, $R_1$, $R_2$, $R_3$ or $R_4$ is selected from H, —OH, —$CH_2OH$, or a C1-C3 alkyl group, and
wherein:
    $R_0$ is different or identical in the n

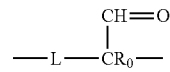

units,
    L is different or identical in the n

units, and $R_1$, $R_2$, $R_3$ or $R_4$ is different or identical in the n

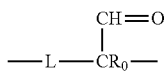

units, respectively.

20. A method of treating human hair to maintain a desired three dimensional structure, said method comprising:
  providing a formulation for crosslinking hair or other keratin fibers, said formulation comprising:
    a crosslinking agent comprising a plurality of oxidized sugars having at least two aldehyde groups or mixture thereof,
    wherein said crosslinking agent is formulated so that the aldehyde groups of the oxidized sugars are effective to react with amine groups of protein molecules contained in a plurality of non-crosslinked hair or other keratin fibers to yield a population of crosslinked hair or other keratin fibers; and
  treating a population of human hair with the formulation so as to maintain the desired three dimensional (3D) structure of the population of human hair, wherein the human hair comprises non-crosslinked protein fibers having protein molecules having amine groups that react with the aldehyde groups of the oxidized sugar of the formulation, and wherein at least 50% of the sugar rings are opened in the oxidized sugar.

21. The method according to claim 20, wherein the formulation is in a form of a paste or an aqueous solution.

22. A method of crosslinking hair or other keratin fibers, said method comprising:
  providing a crosslinking agent comprising an oxidized sugar having at least two aldehyde groups; and
  infiltrating a plurality of non-crosslinked hair or other keratin fibers with the crosslinking agent under conditions effective to cause protein molecules contained in the non-crosslinked hair or other keratin fibers to become crosslinked, thereby yielding a population of crosslinked hair or other keratin fibers,
  wherein the protein molecules of the non-crosslinked hair or other keratin fibers comprise amine groups that react with the aldehyde groups of the oxidized sugar to achieve the crosslinking of the protein molecules to yield the crosslinked hair or other keratin fibers, and
  wherein the oxidized sugar crosslinks the hair or keratin fibers through the reaction between the aldehyde groups of the oxidized sugar and the amine groups of the keratin in hair fibers to form crosslinks, and wherein each oxidized sugar forms at least four covalent bonds linked to one or more molecules within hair or keratin fibers.

* * * * *